(12) United States Patent
Brun et al.

(10) Patent No.: US 9,915,599 B2
(45) Date of Patent: Mar. 13, 2018

(54) MICROPARTICLE ANALYSIS APPARATUS AND MICROPARTICLE ANALYSIS SYSTEM

(71) Applicant: Sony Corporation, Tokyo (JP)

(72) Inventors: Marcaurele Brun, Tokyo (JP); Kazumasa Sato, Tokyo (JP); Shinji Omori, Chiba (JP); Yoichi Katsumoto, Tokyo (JP)

(73) Assignee: Sony Corporation, Tokyo (JP)

( * ) Notice: Subject to any disclaimer, the term of this patent is extended or adjusted under 35 U.S.C. 154(b) by 295 days.

(21) Appl. No.: 14/763,980

(22) PCT Filed: Dec. 26, 2013

(86) PCT No.: PCT/JP2013/084878
§ 371 (c)(1),
(2) Date: Jul. 28, 2015

(87) PCT Pub. No.: WO2014/122873
PCT Pub. Date: Aug. 14, 2014

(65) Prior Publication Data
US 2015/0377763 A1    Dec. 31, 2015

(30) Foreign Application Priority Data
Feb. 8, 2013 (JP) .................... 2013-023374

(51) Int. Cl.
*G01N 15/10* (2006.01)
*G01N 27/22* (2006.01)
(Continued)

(52) U.S. Cl.
CPC ..... *G01N 15/1031* (2013.01); *G01N 15/1218* (2013.01); *G01N 27/221* (2013.01);
(Continued)

(58) Field of Classification Search
CPC .. G01R 33/345; G01R 27/2605; G01R 29/24; G01V 3/02; G01L 1/127;
(Continued)

(56) References Cited

U.S. PATENT DOCUMENTS 5,691,633 A    11/1997   Liu et al.
9,029,724 B2    5/2015   Hashimoto et al.
(Continued)

FOREIGN PATENT DOCUMENTS

JP    63-029267 A    2/1988
JP    07-509560 A    10/1995
(Continued)

OTHER PUBLICATIONS

U.S. Appl. No. 12/472,630, filed May 27, 2009, Hayashi.
(Continued)

*Primary Examiner* — Melissa Koval
*Assistant Examiner* — Trung Nguyen
(74) *Attorney, Agent, or Firm* — Wolf, Greenfield & Sacks, P.C.

(57) ABSTRACT

There is provided a microparticle analysis apparatus including a sample channel configured to receive liquid containing a plurality of microparticles, a first pair of electrodes configured to form an alternating electric field in at least a part of the sample channel, a measuring part configured to measure impedance between the first pair of electrodes, an analyzing part configured to calculate property values of the microparticles from the impedance measured in the measuring part, and a determining part configured to determine whether data of the impedance measured in the measuring part is derived from the microparticles.

17 Claims, 7 Drawing Sheets

(51) Int. Cl.
*G01N 33/487* (2006.01)
*G01N 15/12* (2006.01)
*G01N 15/00* (2006.01)

(52) U.S. Cl.
CPC ............ *G01N 33/48728* (2013.01); *G01N 2015/0065* (2013.01); *G01N 2015/1006* (2013.01); *G01N 2015/1037* (2013.01); *G01N 2015/1081* (2013.01); *G01N 2015/1087* (2013.01); *G01N 2015/129* (2013.01); *G01N 2015/1254* (2013.01)

(58) Field of Classification Search
CPC ......... G01N 2015/129; G01N 15/1031; G01N 2015/1254; G01N 2015/0065
USPC ....... 324/660–688, 600, 500, 444–467, 71.3, 324/71.4, 300, 347, 515
See application file for complete search history.

(56) References Cited

U.S. PATENT DOCUMENTS

| | | | |
|---|---|---|---|
| 9,087,371 | B2 | 7/2015 | Muraki |
| 2001/0032495 | A1 | 10/2001 | Ueno et al. |
| 2011/0192726 | A1* | 8/2011 | Chen .................. G01N 33/5438 204/547 |
| 2011/0269221 | A1 | 11/2011 | Katsumoto et al. |
| 2012/0103813 | A1 | 5/2012 | Sato et al. |
| 2012/0298511 | A1 | 11/2012 | Yamamoto |
| 2013/0256136 | A1 | 10/2013 | Muraki et al. |
| 2013/0258075 | A1 | 10/2013 | Muraki et al. |
| 2014/0087453 | A1 | 3/2014 | Tahara |
| 2014/0144817 | A1 | 5/2014 | Hashimoto et al. |
| 2014/0193059 | A1 | 7/2014 | Muraki |
| 2014/0208875 | A1* | 7/2014 | Muraki .................. B01L 3/502 73/864.81 |
| 2015/0057787 | A1 | 2/2015 | Muraki et al. |
| 2015/0068957 | A1 | 3/2015 | Otsuka et al. |
| 2015/0285726 | A1 | 10/2015 | Tanase et al. |
| 2015/0285727 | A1 | 10/2015 | Muraki |

FOREIGN PATENT DOCUMENTS

| | | |
|---|---|---|
| JP | 2001-305041 A | 10/2001 |
| JP | 2005-512042 A | 4/2005 |
| JP | 2010-181399 A | 8/2010 |
| JP | 2011-112497 A | 6/2011 |
| JP | 2012-098058 A | 5/2012 |
| JP | 2012-098063 A | 5/2012 |
| WO | WO 94/02846 A1 | 2/1994 |
| WO | WO 2011/067961 A1 | 6/2011 |
| WO | WO 2012/003348 A1 | 1/2012 |

OTHER PUBLICATIONS

U.S. Appl. No. 12/733,031, filed Feb. 3, 2010, Katsumoto et al.
U.S. Appl. No. 13/371,881, filed Feb. 13, 2012, Hayashi.
U.S. Appl. No. 14/413,543, filed Jan. 8, 2015, Ito.
U.S. Appl. No. 14/761,667, filed Jul. 17, 2015, Brun et al.
U.S. Appl. No. 14/772,483, filed Sep. 3, 2015, Brun et al.
U.S. Appl. No. 14/772,550, filed Sep. 3, 2015, Hayashi et al.
U.S. Appl. No. 14/775,099, filed Sep. 11, 2015, Katsumoto et al.
U.S. Appl. No. 14/777,906, filed Sep. 17, 2015, Brun et al.
U.S. Appl. No. 14/778,277, filed Sep. 18, 2015, Hayashi et al.
U.S. Appl. No. 15/028,419, filed Apr. 8, 2016, Muraki et al.
U.S. Appl. No. 15/093,879, filed Apr. 8, 2016, Muraki et al.

* cited by examiner

MICROPARTICLE ANALYSIS APPARATUS AND MICROPARTICLE ANALYSIS SYSTEM

CROSS REFERENCE TO RELATED APPLICATIONS

This application claims the benefit under 35 U.S.C. § 371 as a U.S. National Stage Entry of International Application No. PCT/JP2013/084878, filed in the Japanese Patent Office as a Receiving Office on Dec. 26, 2013, which claims priority to Japanese Patent Application Number JP2013-023374, filed in the Japanese Patent Office on Feb. 8, 2013, each of which applications is hereby incorporated by reference in its entirety.

TECHNICAL FIELD

The present technology relates to microparticle analysis apparatuses and microparticle analysis systems. More particularly, the present technology relates to a microparticle analysis apparatus and a microparticle analysis system for identifying individual microparticles according to differences in electrical properties.

BACKGROUND ART

As is well known, microparticles such as cells typically have different physical property values indicating electrical properties such as conductivity, dielectric constant, and permittivity, depending on the type, the conditions, and the like of the microparticles. For example, the conductivity of extracellular fluid and intracellular fluid for muscle cells and nerve cells is higher than that for skin cells with less moisture. Furthermore, in the measurement of the dielectric constant of cells by frequency sweep, the dielectric relaxation properties change with the form of the cells.

In the related art, an apparatus for detecting the impedance of microparticles flowing between a pair of electrodes disposed in a channel has been proposed as a technique for identifying individual microparticles according to such electrical properties (see Patent Literature 1). In addition, dielectric cytometry apparatuses for measuring the dielectric spectrum of microparticles flowing in a microchannel have been also proposed (see, for example, Patent Literatures 2 and 3).

In the dielectric cytometry apparatus described in Patent Literature 2, a fluid device having a narrow part in a channel and electrodes adjacent to the narrow part is used to improve the measurement accuracy. In the dielectric cytometry apparatus described in Patent Literature 3, a branched path is provided downstream of a narrow part in a channel of a fluid device, an electric field is applied to cells that have passed through the narrow part based on the information on the complex dielectric constant measured, and the direction of cell flow is controlled by dielectrophoresis to sort the cells.

CITATION LIST

Patent Literature

Patent Literature 1: JP 2005-512042T
Patent Literature 2: JP 2010-181399A
Patent Literature 3: JP 2012-098063A

SUMMARY OF INVENTION

Technical Problem

The dielectric cytometry described above is a very effective technique in life science research fields including regenerative medicine and immunology or in medical fields including clinical examinations because the dielectric cytometry can analyze and sort microparticles without labeling substances. Dielectric cytometry apparatuses known in the art, however, tend to have reduced measurement accuracy due to noise or the like because a sample liquid containing multiple microparticles is allowed to flow in a microchannel and the complex dielectric constant is measured during the passage of the microparticles between a pair of electrodes. For this, there is a need for further improving the measurement accuracy of dielectric cytometry apparatuses.

Solution to Problem

Therefore, a main object of the present disclosure is to provide a microparticle analysis apparatus and a microparticle analysis system that can accurately identify and sort individual microparticles without using a labeling substance.

A microparticle analysis apparatus according to the present disclosure includes: a sample channel configured to receive liquid containing a plurality of microparticles; a first pair of electrodes configured to form an alternating electric field in at least a part of the sample channel; a measuring part configured to measure impedance between the first pair of electrodes; an analyzing part configured to calculate property values of the microparticles from the impedance measured in the measuring part; and a determining part configured to determine whether data of the impedance measured in the measuring part is derived from the microparticles.

The determining part may detect passage of the microparticles through the alternating electric field from the data of the impedance, and may make determination based on a detection result.

In that case, the determining part can detect the passage of the microparticles from a peak position and a peak height of conductance obtained from the impedance.

Alternatively, the determining part can start detecting the passage of the microparticles when a value/values of capacitance and/or conductance obtained from the impedance is/are over a threshold, and the determining part can stop detecting the passage of the microparticles when the value/values is/are less than or equal to the threshold.

The determining part can also determine that the data of the impedance is derived from the microparticles only when the value/values of the capacitance and/or the conductance is/are over the threshold for a predetermined period.

The analyzing part may calculate the property values for the data that is determined to be derived from the microparticles in the determining part.

In this case, the analyzing part may calculate the property values by comparison or fitting of the data measured in the measuring part with a particular model.

The particular model can use, for example, a dielectric relaxation phenomenon model based on a complex dielectric spectrum.

The microparticle analysis apparatus may include a sorting part configured to sort the microparticles based on the property values calculated in the analyzing part.

In this case, a second pair of electrodes configured to form an electric field downstream of an area where the alternating electric field is formed in the sample channel may be included. The electric field formed by the second pair of electrodes may generate dielectrophoresis to change a flow direction of the microparticles.

Two or more branched channels in communication with the sample channel can be included. The sorting part can change the flow direction of the microparticles, and the microparticles can be introduced to any of the branched channels.

Meanwhile, the sample channel may include a narrow part, and the first pair of electrodes are disposed to sandwich the narrow part.

An imaging part configured to image the microparticles passing through the alternating electric field may be included.

The microparticles may be cells.

The property values can include at least one value selected from the group consisting of membrane capacitance, conductivity of cytoplasm, and particle size.

The measuring part may measure complex impedance at multiple points within a frequency range from 0.1 to 50 MHz.

A microparticle analysis system according to the present disclosure includes: a microparticle analysis apparatus including a sample channel configured to receive liquid containing a plurality of microparticles, a first pair of electrodes configured to form an alternating electric field in at least a part of the sample channel, and a measuring part configured to measure impedance between the first pair of electrodes; and an information processor including an analyzing part configured to calculate property values of the microparticles from the impedance measured in the measuring part, and a determining part configured to determine whether data of the impedance measured in the measuring part is derived from the microparticles.

The microparticle analysis system may further include: a display configured to display the property values of the microparticles calculated in the analyzing part of the information processor.

A server including an information storage part configured to store the property values of the microparticles calculated in the analyzing part of the information processor may be included.

Advantageous Effects of Invention

According to the present disclosure, individual microparticles can be accurately identified and sorted without using a labeling substance.

BRIEF DESCRIPTION OF DRAWINGS

FIG. 3A is a perspective view and FIG. 3B is a cross-sectional view taken along the line a-a.

FIG. 4A is a perspective view and FIG. 4B is a cross-sectional view taken along the line b-b.

DESCRIPTION OF EMBODIMENTS

Hereinafter, embodiments of the present disclosure will be described in detail with reference to the appended drawings. It should be understood that the present disclose is not limited to the embodiments described below. The description is made in the following order.

1 First Embodiment
(Exemplary microparticle analysis apparatus including determining part)
2. Modification of First Embodiment
(Exemplary microparticle analysis apparatus including analyzing part that also functions as determining part)
3. Second Embodiment
(Exemplary microparticle sorting apparatus including determining part)
4. Third Embodiment
(Exemplary microparticle analysis system)

1. First Embodiment

Figure 1:
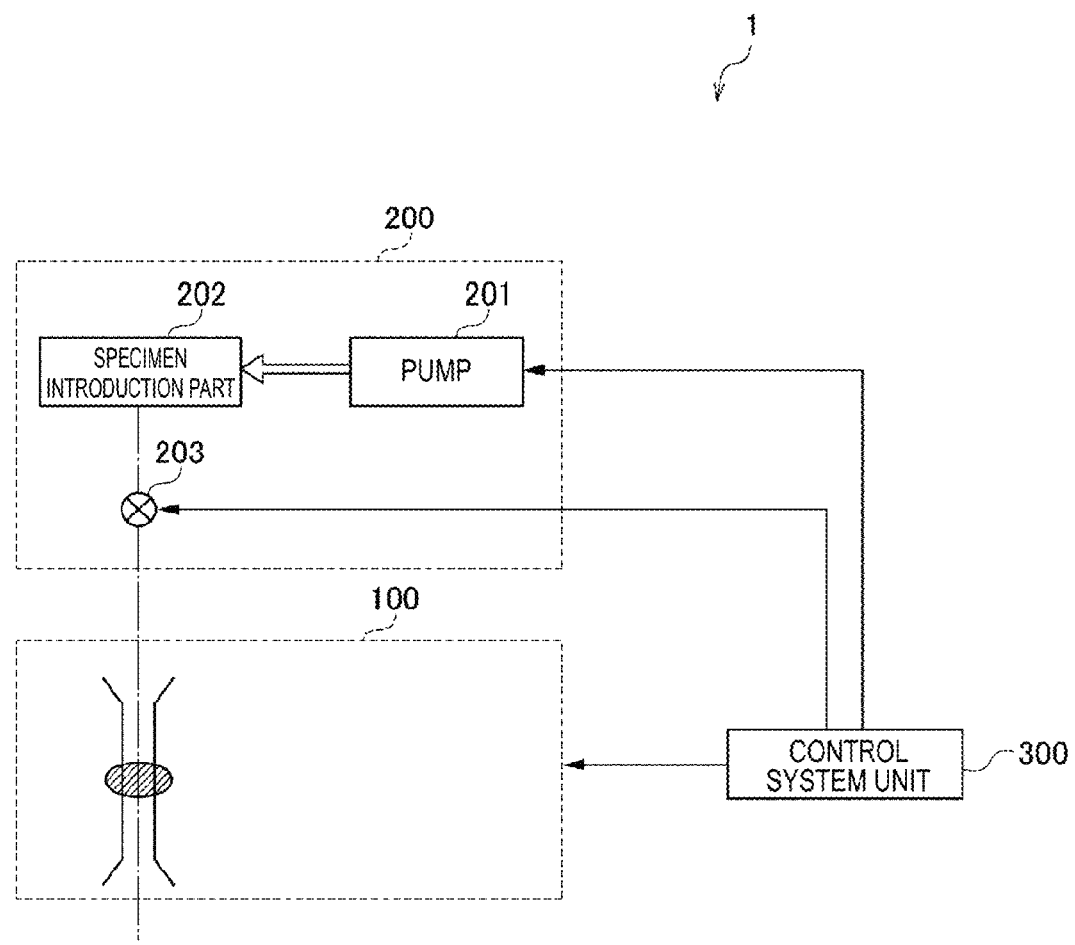
FIG. 1 is a diagram illustrating a schematic configuration of a microparticle analysis apparatus according to a first embodiment of the present disclosure.

First, description is made on a microparticle analysis apparatus according to a first embodiment of the present disclosure. FIG. 1 is a diagram illustrating a schematic configuration of a microparticle analysis apparatus according to the present embodiment. As shown in FIG. 1, a microparticle analysis apparatus 1 according to the present embodiment includes a measurement system unit 100, a flow forming system unit 200, and a control system unit 300 that controls the units 100 and 200.

(Measurement System Unit 100)

Figure 2:
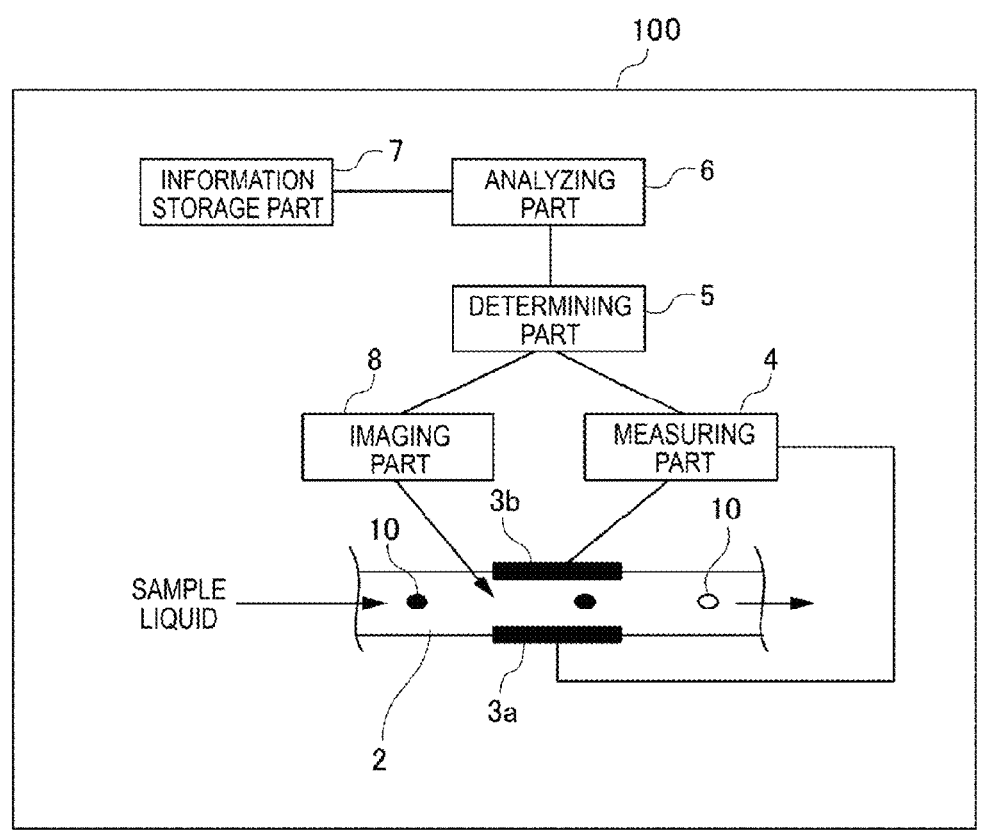
FIG. 2 is a diagram illustrating a schematic configuration of a measurement system unit 100 shown in FIG. 1.

FIG. 2 is a diagram illustrating a schematic configuration of the measurement system unit 100 shown in FIG. 1. As shown in FIG. 2, the measurement system unit 100 includes a sample channel 2, a pair of electrodes composed of an electrode 3a and an electrode 3b, a measuring part 4, a determining part 5, an analyzing part 6, and optionally an information storage part 7 and an imaging part 8. In the microparticle analysis apparatus 1, a sample liquid containing multiple microparticles 10 is introduced to the sample channel 2, and the impedance of each microparticle 10 is measured in the measuring part 4.

[Microparticles 10]

Here, examples of the microparticles 10 that are measured in the microparticle analysis apparatus 1 according to the present embodiment may include cells, biologically-relevant microparticles such as microbes, ribosomes and the like, and artificial particles such as latex particles, gel particles, and industrial particles.

Further, the biologically-relevant microparticles may also be the chromosomes, ribosomes, mitochondria, organelles and the like that form various types of cells. In addition, examples of cells include plant cells, animal cells, hematopoietic cells and the like. Still further, examples of microbes include bacteria such as *E. coli*, viruses such as the tobacco mosaic virus, fungi such as yeast and the like. The term biologically-relevant microparticles also includes biologically-relevant polymers such as nucleic acids, proteins, and complexes thereof.

On the other hand, examples of industrial particles include particles formed from an organic polymeric material, an inorganic material, a metal material and the like. As an organic polymeric material, polystyrene, styrene-divinylbenzene, polymethyl methacrylate and the like may be used. As an inorganic material, glass, silica, magnetic materials and the like may be used. As a metal material, for example, a metal colloid, aluminum and the like can be used. It is noted that although the shape of these microparticles is usually spherical, these microparticles may have a non-spherical shape. Further, the size, mass and the like of these microparticles is also not especially limited.

[Sample Channel 2]

Figure 3:
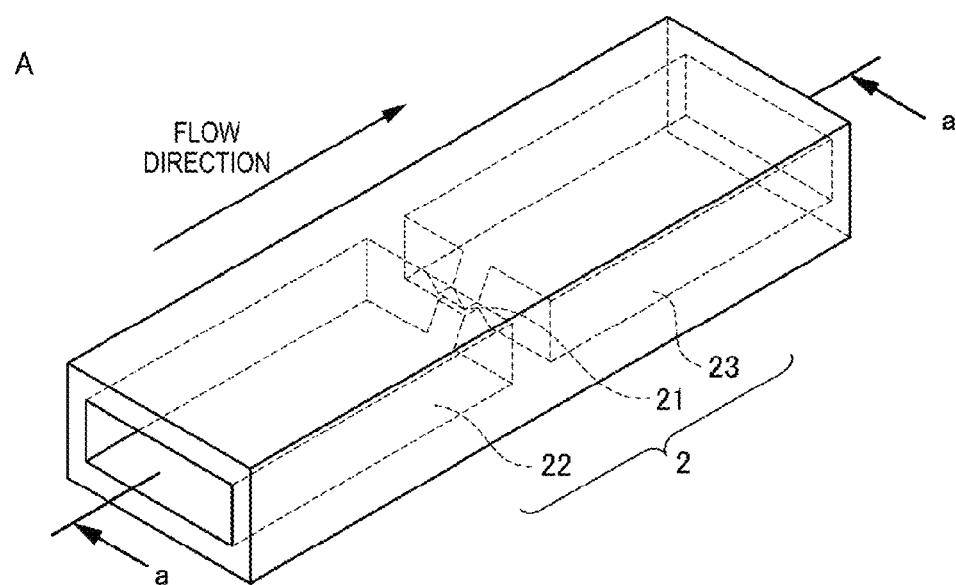
FIGS. 3A and 3B are schematic diagrams illustrating configuration examples of a sample channel 2 shown in FIG. 2, where
Figure 3:
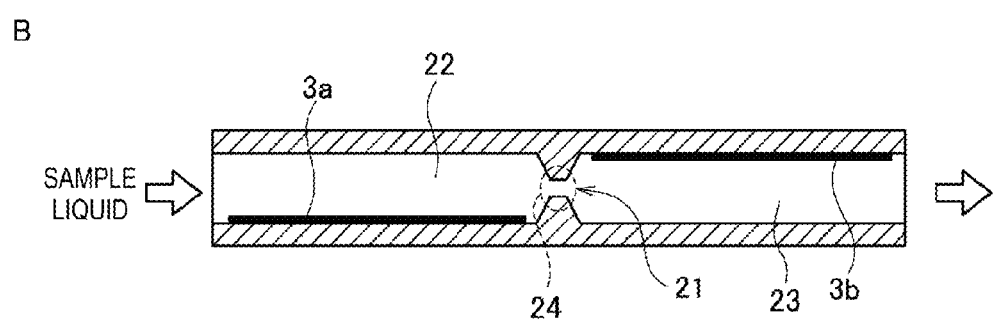
Figure 4:
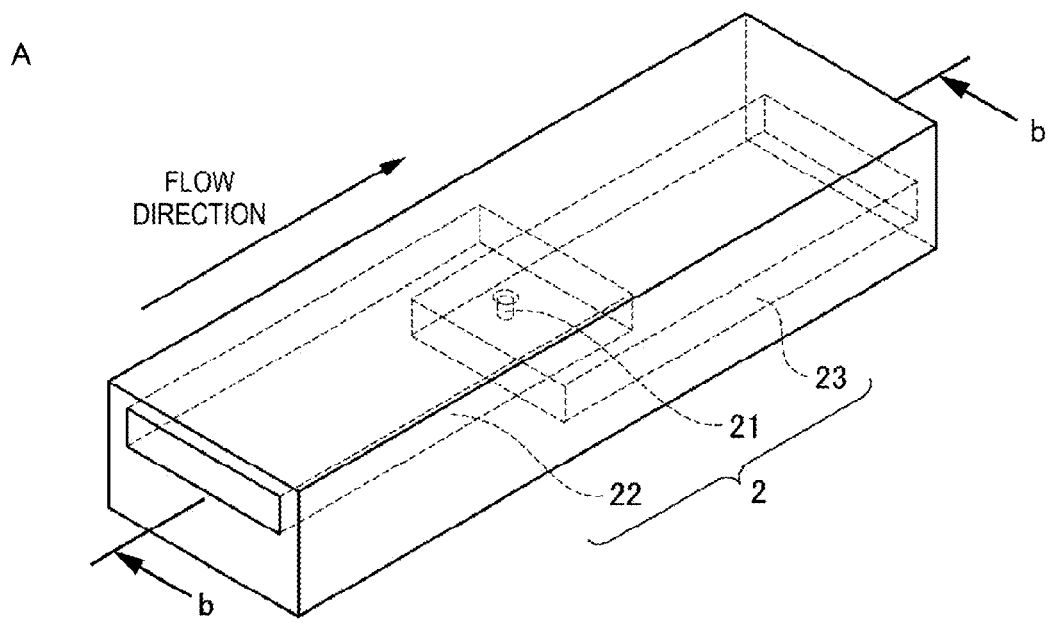
FIGS. 4A and 4B are schematic diagrams illustrating other configuration examples of the channel 2 shown in FIG. 2, where
Figure 4:
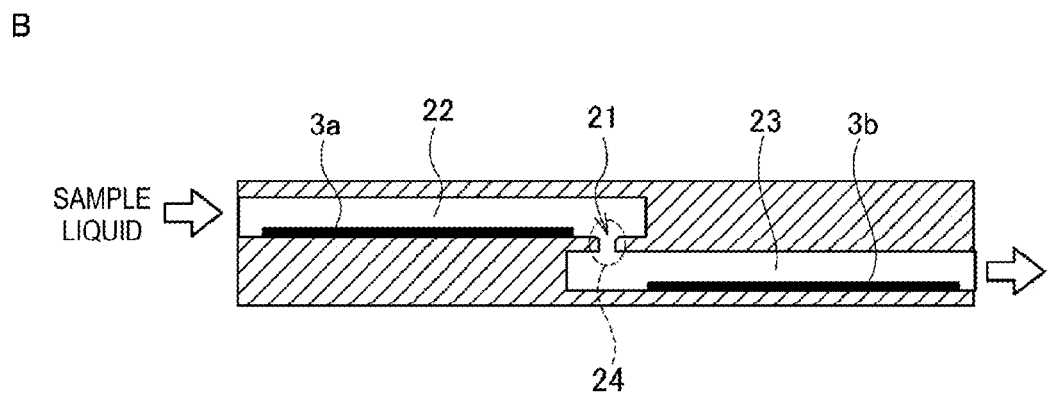

The sample channel 2 is formed, for example, in a microchip. The sample channel 2 is formed from any material that has insulation properties and no effect on the electrical properties of the target microparticles 10. Specific examples of materials include plastic materials, such as polycarbonate, cycloolefin polymer, polypropylene, and polyimide; polydimethylsiloxane (PDMS); and glass. Of these materials, insulating plastic materials, such as polyimide, are preferably used because of easy formation of electrodes and good mass productivity FIGS. 3 and 4 are schematic diagrams illustrating configuration examples of the sample channel 2. As shown in FIGS. 3 and 4, the sample channel 2 has a narrow part 21 through which the microparticles 10 can pass, and the impedance of the microparticles 10 is measured in the narrow part 21. The size of the narrow part 21 is sufficient for each target microparticle 10 to pass through, and can be appropriately set according to the particle size of the microparticles 10 or the like. The narrow part 21 thus provided in an impedance measurement area 24 can significantly reduce the contribution of electric double layer capacitance and thus can decrease the influence of electrode polarization responsible for noise to increase measuring sensitivity.

The sample channel 2 includes the narrow part 21, an inflow channel part 22 upstream of the narrow part 21, and an outflow channel part 23 downstream of the narrow part 21, wherein the parts 21, 22 and 23 may be coaxially aligned as shown in FIG. 3, or may be out of alignment in the thickness direction as shown in FIG. 4. In particular, when the inflow channel part 22, the narrow part 21, and the outflow channel part 23 are out of alignment in the thickness direction as shown in FIG. 4, the base in the channel part becomes thick to improve the pressure resistance. The configuration illustrated in FIG. 4 is produced by bonding channel-formed parts and parts in which a channel is not substantially formed, which facilitates channel formation and bonding to reduce the production cost, as compared with the configuration illustrated in FIG. 3.

The sample channel 2 may include an injection hole through which the target microparticles 10 are injected separately from a solvent constituting a sample liquid. In this case, a liquid containing the target microparticles 10 (for example, a specimen, a blood sample, or the like with the cell concentration adjusted by dilution with a medium) may be injected through the injection hole while a solvent, such as physiological saline, is allowed to flow in the sample channel 2. This eliminates the need for preparing a sample liquid containing the target microparticles 10 in advance to improve the working efficiency.

[Electrodes 3a and 3b]

The electrodes 3a and 3b are intended to form an alternating electric field in at least a part of the sample channel 2 and for example, are disposed to sandwich the narrow part 21, as shown in FIGS. 3 and 4. The electrodes 3a and 3b are made from any material that has a little influence on the microparticles 10.

Although the configuration according to the present embodiment includes a pair of electrodes in the impedance measurement area 24, the present disclosure is not limited to this configuration and multiple pairs of electrodes may be provided in the impedance measurement area 24. The multiple pairs of electrodes provided in the impedance measurement area 24 enable, for example, detection by 4-terminal sensing to improve the accuracy of impedance measurement.

[Measuring Part 4]

The measuring part 4 applies alternating voltage between the electrode 3a and the electrode 3b described above and measures the impedance of each microparticle 10 that passes through the alternating electric field thus formed. The measuring part 4 has any configuration that enables measurement of the impedance of each microparticle 10, and for example, the measuring part 4 may include one or two or more impedance analyzers or network analyzers.

At this time, the impedance may be measured at multiple frequencies by changing the frequency of the alternating voltage applied between the electrode 3a and the electrode 3b or by superimposing multiple frequencies to obtain the complex dielectric spectrum of each microparticle 10. Specific methods thereof include arrangement of multiple single-frequency analyzers, frequency sweep, superimposition of frequencies and subsequent extraction of the information at each frequency through a filter, and measurement of impulse response.

[Determining Part 5]

The determining part 5 determines whether data of the impedance measured in the measuring part 4 described above is derived from the microparticles 10. The data of the impedance measured in the measuring part 4 contains noise components in addition to the information derived from the target microparticles 10. In the microparticle analysis apparatus of the present embodiment, the determining part 5 determines whether the impedance data measured in the measuring part 4 is derived from the microparticles 10 to improve the accuracy of the analysis results finally obtained.

The determining part 5, for example, detects the passage of the microparticles 10 through the alternating electric field according to the impedance data measured in the measuring part 4, and makes determination based on the detection results. The method for detecting the passage of the microparticles 10 through the alternating electric field is not limited to any particular method, but examples thereof may include detection based on the peak position, peak height, and peak width of the conductance or capacitance obtained from the impedance, and combinations thereof.

The determining part 5 may start detecting the passage of the microparticles 10 when the value/values of the conductance and/or capacitance obtained from the impedance is/are over the threshold, and may stop detecting the passage of the microparticles 10 when the value/values of the conductance and/or capacitance is/are less than or equal to the threshold. In this case, the determining part 5 determines that the impedance data is derived from the microparticles 10 only when the value/values of the capacitance and/or conductance is/are over the threshold for a predetermined period.

[Analyzing Part 6]

The analyzing part 6 performs comparison or fitting of the impedance data determined to be derived from the microparticles 10 in the determining part 5, the dielectric spectrum calculated from the impedance data, or the like with particular model types such as dielectric relaxation phenomenon model to give the property values of the microparticles 10. When, for example, the target microparticles 10 are cells, the property values calculated in the analyzing part 6 include various structural parameters regarding the microparticles 10, such as membrane capacitance, conductivity of cytoplasm, particle size, nuclear size, and thickness of nuclear membrane.

[Information Storage Part 7]

The information storage part 7 stores the property values obtained in the analyzing part 6, and the impedance data and complex dielectric spectrum measured in the measuring part 4. This information storage part 7 may not be necessarily provided in the apparatus, and may be provided in an externally-connected hard disk, server, or the like.

[Imaging Part 8]

The microparticle analysis apparatus of the present embodiment may include the imaging part 8 configured to image the microparticles 10 passing through the alternating electric field formed by the electrodes 3a and 3b or the narrow part 21 in the sample channel 2. The configuration of the imaging part 8 is not limited to any particular configuration, and optical systems including an image sensor, such as a charge coupled device (CCD) and a complementary metal oxide semiconductor (CMOS), can be used. The data captured by the imaging part 8 is used to, for example, check the passage of the microparticles 10 on the image in the determining part 5 or the analyzing part 6.

(Flow Forming System Unit 200)

The flow forming system unit 200 is intended to introduce a sample liquid containing the multiple microparticles 10 to the sample channel 2 of the measurement system unit 100, and includes a pump 201, a specimen introduction part 202, and a valve 203. In the flow forming system unit 200, application of pressure to the specimen introduction part 202, for example, by pump 201 allows the sample liquid injected into the specimen introduction part 202 to be introduced to the sample channel 2 of the measurement system unit 100 through the valve 203.

The valve 203 can be opened and closed and the opening and closing are controlled by the control system unit 300 described below. The flow forming system unit 200 may further include a flowmeter, a temperature sensor, and a pressure sensor.

(Control System Unit 300)

The control system unit 300 is intended to control the measurement system unit 100 and the flow forming system unit 200 described above. The control system unit 300 controls the pressure of the pump 201 and the opening size of the valve 203 in the flow forming system unit 200, for example, based on the information inputted through the input interface, thereby adjusting the flow amount and flow rate of the sample liquid flowing through the sample channel 2 of the measurement system unit 100.

(Others)

The microparticle analysis apparatus 1 of the present embodiment may also include: a display part configured to display the impedance data measured in the measuring part 4, the results determined in the determining part 5, and the dielectric spectrum and various property values calculated in the analyzing part 6, in the measurement system unit 100; and an output part configured to output them to various media. The microparticle analysis apparatus 1 of the present embodiment may include an information input part through which a user inputs the selected information of the display data and the information on test specimens.

[Operation]

Next, the operation of the microparticle analysis apparatus of the present embodiment, that is, the method for analyzing the microparticles 10 using the microparticle analysis apparatus 1 will be described. In the microparticle analysis apparatus 1 of the present embodiment, a sample liquid containing the microparticles 10 is allowed to flow in the sample channel 2. Alternatively, while a solvent, such as physiological saline, flows in the sample channel 2, a liquid containing the microparticles is injected into the sample channel 2 and thus allowed to flow together with the solvent.

In this case, the flow amount (flow rate) of the sample liquid is not limited to any particular amount, and can be appropriately set according to the diameter of the channel or the narrow part, the size of the microparticles 10, the number of pieces of data acquired, and the like. From the viewpoint of the accuracy of detection and sorting, the flow amount of the sample liquid is preferably about the flow amount sufficient for the microparticles 10 to be present in the narrow part of the sample channel 2 for twice or more as longer time as the measurement interval for the impedance in the measuring part 4. This can reduce the influence of the flow amount of the sample liquid on the measured results. It is noted that the flow amount of the sample liquid can be adjusted with a pressure regulator of a liquid delivery unit or the like.

The measuring part 4 applies alternating voltage between the electrodes 3a and 3b continuously or at the time of passage of the microparticles 10 to form an alternating electric field in the sample channel 2. The measuring part 4 then measures the impedance of the microparticles 10 at the passage of the microparticles 10 through the alternating electric field. For example, in order to check the dielectric relaxation phenomenon of the microparticles 10, which are cells, the complex impedance may be measured at multiple points within the frequency range from 0.1 to 50 MHz.

In the microparticle analysis apparatus of the present embodiment, as desired, the imaging part 8 images the microparticles 10 passing through the alternating electric field formed by the electrodes 3a and 3b or the narrow part 21 in the sample channel 2, in combination with impedance measurement in the measuring part 4.

Next, the determining part 5 detects the passage of the microparticles 10 through the alternating electric field according to the data of the impedance measured in the measuring part 4, and determines whether the data of the measured impedance is derived from the microparticles 10 based on the detection results. Specifically, the determining part 5 determines that the data when the passage of the microparticles 10 is detected is derived from the microparticles 10, and that the data when the passage of the microparticles 10 is not detected is derived from noise or the like.

In this case, the method for detecting the passage of the microparticles 10 is not limited to any particular method, but for example, the passage of the microparticles 10 can be detected using the value of the conductance obtained from the impedance measured in the measuring part 4. When no microparticles 10 are present in the alternating electric field (the impedance measurement area 24), the value of the conductance varies at about a level of noise width around a given mean value. On the other hand, when the microparticles 10 pass through the alternating electric field (the impedance measurement area 24), the value of the conductance decreases to a given minimum value and then increases to a baseline again.

Therefore, given that the time from the start of falling to the end of rising from/to the baseline indicates the passage of the microparticles 10, the passage of the microparticles 10 can be detected from the peak position and the peak height.

In addition, the passage of the microparticles 10 can be also detected using combination of the conductance data and the capacitance data. The passage of the microparticles 10 through the alternating electric field (the impedance measurement area 24) generates a positive capacitance peak and a negative conductance peak. The detection of these peaks enables detection of the passage of the microparticles 10.

In this method, preferably the determining part 5 starts detecting the passage of the microparticles 10 when the value/values of the conductance and/or capacitance obtained from the impedance measured in the measuring part 4 is/are over the threshold, and stops detecting the passage of the microparticles 10 when the value/values of the conductance and/or capacitance is/are less than or equal to the threshold. That is, when the value/values of the capacitance and/or conductance is/are less than or equal to the threshold, it is not determined that the peak is derived from the passage of the microparticles 10. This can prevent the change in value due to noise from being detected as a peak derived from the passage of the microparticles 10.

In this method, only when the value/values of the capacitance and/or conductance is/are over the threshold for a predetermined period, the detected peak is recognized to be derived from the passage of the microparticles 10 and the data of the impedance is determined to be derived from the microparticles 10. This can further improve the accuracy in detection of the passage of the microparticles 10.

In the microparticle analysis apparatus 1 of the present embodiment, the passage of the microparticles 10 can be checked based on the image data captured in the imaging part 8, in combination with detection of the passage of the microparticles 10 in the determining part 5.

In the microparticle analysis apparatus 1 of the present embodiment, the property values, such as complex dielectric spectrum, dielectric relaxation, membrane capacitance, conductivity of cytoplasm, and particle size, are calculated in the analyzing part 6 for the data determined to be derived from the microparticles 10 by the determining part 5. The methods for calculating these property values are not limited to particular methods, and can be various calculation methods, such as comparison and fitting with particular model types.

Specifically, the impedance data determined to be derived from the microparticles 10 in the determining part 5 is first corrected, followed by smoothing, and then the complex dielectric constant at each frequency is obtained using Debye's formula. This provides the properties of dielectric relaxation, such as dielectric relaxation strength $D_e$, dielectric relaxation time $\tau_a$, and dielectric relaxation frequency $f_a$. To reduce the processing time, the complex dielectric constant can be calculated without correction or smoothing.

For example, the particle size (diameter) d of the microparticles 10 can be calculated from the value of the conductance $G_{low}$, at a frequency lower than that of the dielectric relaxation. The membrane capacitance $C_m$ can be calculated from the particle size d and the relaxation strength $D_e$, and the cytoplasm electrical conductivity K can be calculated from the membrane capacitance $C_m$, the particle size d, and the relaxation frequency $f_a$.

In the microparticle analysis apparatus 1 of the present embodiment, the microparticles 10 are identified based on the property values calculated in the analyzing part 6 followed by sorting, evaluation on the conditions, and the like. The property values calculated in the analyzing part 6 and the data of the impedance measured in the measuring part 4 are stored in the information storage part 7, and can be displayed on the display part (not shown), outputted as data, or printed according to the user's request.

As described above in detail, the microparticle analysis apparatus 1 of the present embodiment eliminates the need for using a labeling substance because the microparticle analysis apparatus 1 identifies the individual microparticles according to the values of the electrical properties calculated from the impedance of the microparticles. The determining part configured to determine whether the data of the impedance is derived from the microparticles is provided to reduce the influence of noise or the like. This results in accurate identification of the individual microparticles without using a labeling substance.

It is noted that the microparticle analysis apparatus 1 of the present embodiment can also analyze the microparticles using a labeling substance in the same manner as apparatuses known in the art.

2. Modification of First Embodiment

Figure 5:
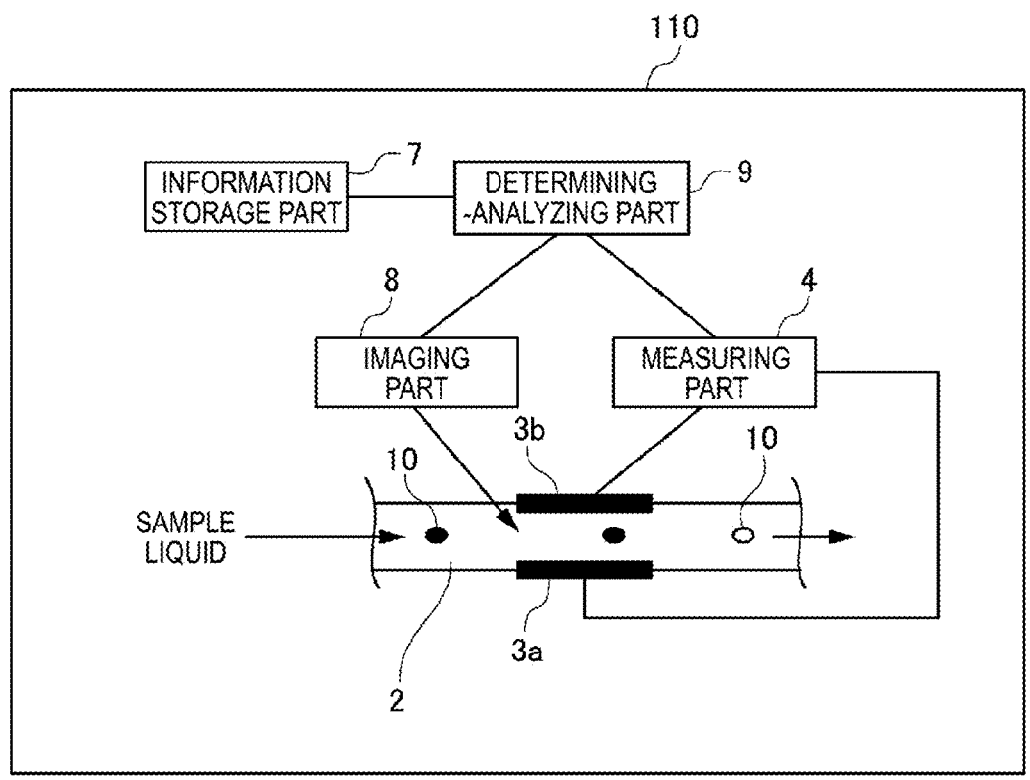
FIG. 5 is a diagram illustrating a schematic configuration of a measurement system unit of a microparticle analysis apparatus according to a modification of the first embodiment of the present disclosure.

Next, description is made on a microparticle analysis apparatus according to a modification of the first embodiment of the present disclosure. FIG. 5 is a diagram illustrating a schematic configuration of a measurement system unit of a microparticle analysis apparatus according to this modification. In FIG. 5, the same elements as in the measuring unit 100 shown in FIG. 2 are designated by the same numerals, and a detailed description thereof is omitted here.

Although the determining part and the analyzing part are provided separately in the first embodiment described above, the present disclosure is not limited to this configuration and the analyzing part may also make determination. In the microparticle analysis apparatus of this modification, as shown in FIG. 5, a determining-analyzing part 9 is provided in a measurement system unit 110. The determining-analyzing part 9 determines whether the data of the impedance measured in a measuring part 4 is derived from the microparticles 10 and calculates the property values.

In this case, the method for determining whether the data is derived from the microparticles 10 is not limited to any particular method but for example, determination can be made based on the complex dielectric constant spectrum calculated from the data of the impedance measured in the measuring part 4.

The microparticle analysis apparatus of this modification can also reduce the influence of noise or the like as in the first embodiment described above and accordingly can accurately identify the individual microparticles without using a labeling substance. The configuration, operation, and effects of the microparticle analysis apparatus of this modification other than those described above are the same as those in the first embodiment described above.

3. Second Embodiment

Figure 6:
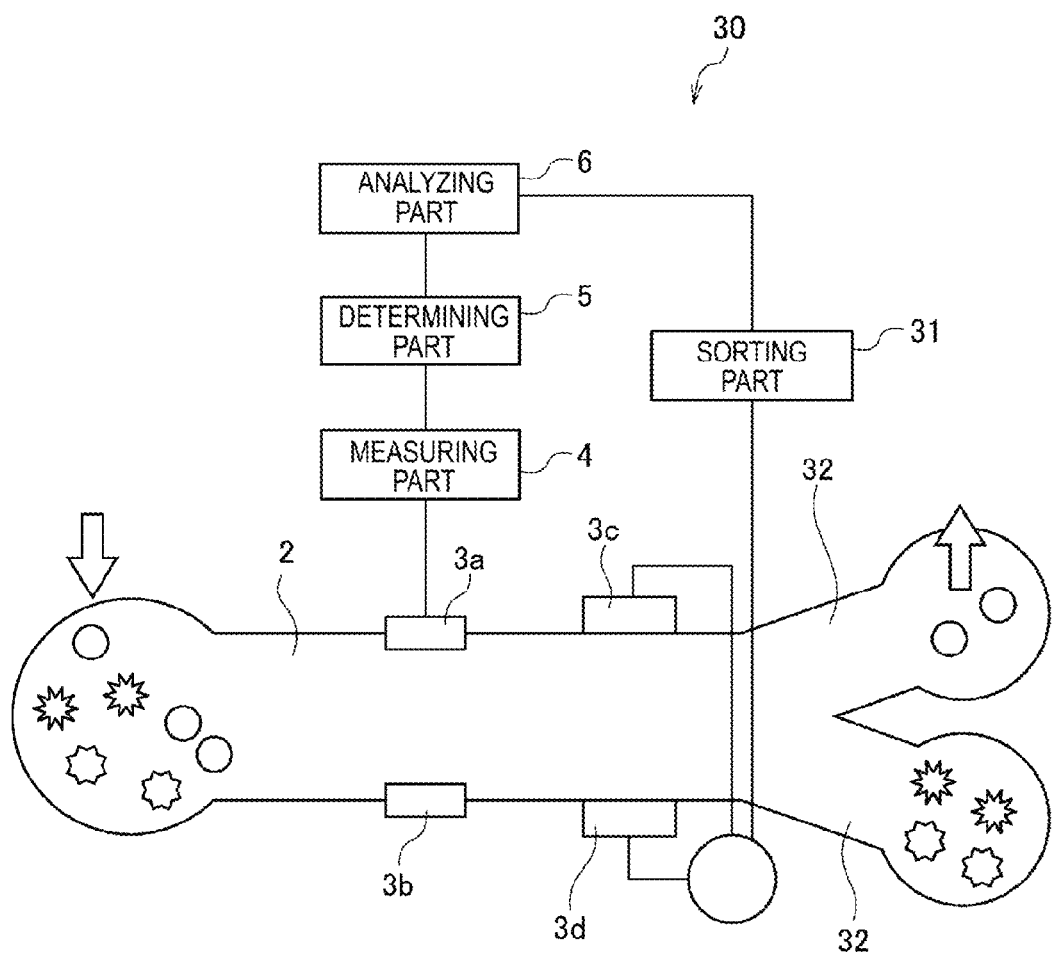
FIG. 6 is a diagram illustrating a schematic configuration of a microparticle sorting device according to a second embodiment of the present disclosure.

Next, description is made on a microparticle sorting device according to a second embodiment of the present disclosure. FIG. 6 is a diagram illustrating a schematic configuration of the microparticle sorting device according to the present embodiment. In FIG. 6, the same elements as in the microparticle analysis apparatus 1 shown in FIG. 1 are designated by the same numerals, and a detailed description thereof is omitted here. As shown in FIG. 6, a microparticle sorting device 30 of the present embodiment includes a pair of electrodes (electrodes 3c and 3d) downstream of an impedance measuring part in a sample channel 2 and a sorting part 31.

[Electrodes 3c and 3d]

The electrodes 3c and 3d are intended to form an electric field downstream of the impedance measurement area in the sample channel 2. The electrodes 3c and 3d are made from any material that has a little influence on the microparticles 10. Although the pair of electrodes are provided downstream of an impedance measurement area 24 in FIG. 6, the present disclosure is not limited to this configuration and multiple pairs of electrodes may be provided in this area. The multiple pairs of electrodes provided downstream of the impedance measurement area 24 increases the number of particles that can be present at the same time in an operating part to improve the processing capacity per unit time and enable fine adjustment of the flow direction of the microparticles 10.

[Sorting Part 31]

The sorting part 31 controls the flow direction of the microparticles 10 by controlling electric field formation based on the property values calculated in the analyzing part 6. For example, as shown in FIG. 6, two or more branched channels 32 in communication with the sample channel 2 are provided. The sorting part 31 changes the flow direction of the microparticles 10 by controlling the voltage value applied between the electrode 3c and the electrode 3d or whether the voltage is applied, and accordingly introduces the microparticles to the corresponding branched channels 32. Then, the installation of the sample channel 2 and the branched channels 32 in a microchip allows analysis and sorting in the microchip.

[Operation]

Next, the operation of the microparticle sorting device 30 of the present embodiment, that is, the method for sorting the microparticles 10 using the microparticle sorting device 30 will be described. In the microparticle sorting device 30 of the present embodiment, a sample liquid containing the target microparticles 10 is allowed to flow in the sample channel 2. The measuring part 4 then measures the impedance of the microparticles 10 by applying alternating voltage between the electrodes 3a and 3b continuously or at the time of passage of the microparticles 10 to form an alternating electric field in the sample channel 2.

The determining part 5 determines whether the data of the impedance measured in the measuring part 4 is derived from the microparticles 10 and then the analyzing part 6 calculates the property values. Thereafter, the microparticles 10 are identified and sorted based on the property values calculated in the analyzing part 6. At this time, the sorting part 31 applies a predetermined voltage between the electrode 3c and the electrode 3d according to the property values (the results of identification) calculated in the analyzing part 6 to form an electric field. This generates dielectrophoresis force, which can guide the microparticles 10 to the corresponding branched channels 32.

In the microparticle sorting device of the present embodiment, the determining part configured to determine whether the data of the impedance is derived from the microparticles is provided to reduce the influence of noise the like. This results in accurate identification and sorting of the individual microparticles without using a labeling substance.

Dielectric cytometry apparatuses known in the art had neither algorithm nor system capable of peak detection and determination in real time. For this, feature points were not extracted from the measured data in real time. Even if the microparticles were sorted based on the value of the measured dielectric constant, they were not sorted according to, for example, the features of the dielectric spectrum.

On the other hand, the microparticle sorting device of the present embodiment can extract feature points in real time, so that the microparticles are not distinguished according to the value of the dielectric constant but can be distinguished based on the feature values, such as dielectric relaxation properties and particle size. This improves the sorting accuracy of the microparticle sorting device of the present embodiment as compared with devices known in the art.

When, for example, the microparticles 10 are cells, the microparticles 10 can be sorted by gating according to the membrane capacitance $C_m$, the cytoplasm electrical conductivity K, the particle size d, and the like that are calculated in the analyzing part 6. Since the microparticle sorting device of the present embodiment can be sorted without labeling living cells, the sorted cells can be recycled. The configuration and effects other than those described above in the present embodiment are the same as those in the first embodiment described above.

4. Third Embodiment

Figure 7:
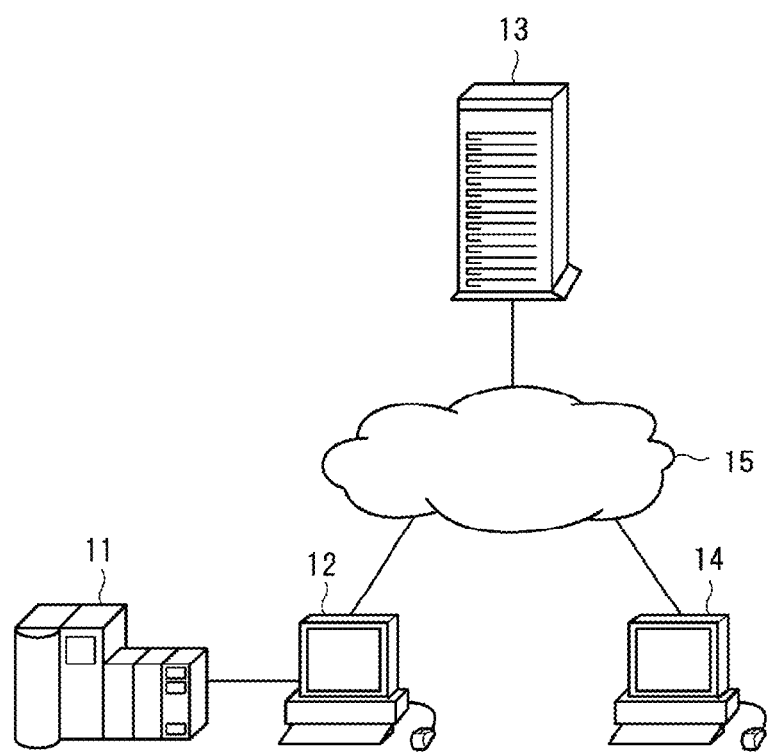
FIG. 7 is a diagram illustrating a schematic configuration of a microparticle analysis system according to a third embodiment of the present disclosure.

Next, description is made on a microparticle analysis system according to a third embodiment of the present disclosure. FIG. 7 is a diagram illustrating a schematic configuration of a microparticle analysis system according to the present embodiment. The microparticle analysis apparatus of the first embodiment described above calculates the property values of the microparticles and makes determination of the data of the measured impedance in the device. Such processing, however, can be performed in one or two or more information processors connected to the analysis apparatus.

Specifically, as shown in FIG. 7, the microparticle analysis system of the present embodiment includes one or two or more information processors 12 separated from the microparticle analysis apparatus 11. In addition, the microparticle analysis system of the present embodiment may be connected to a server 13, a display 14, or the like as desired.

[Microparticle Analysis Apparatus 11]

The microparticle analysis apparatus 11 includes: a sample channel; a pair of electrodes configured to form an alternating electric field in at least a part of the sample channel; and a measuring part configured to measure the impedance between the pair of electrodes. The specific configuration and operation of the sample channel, the pair of electrodes, and the measuring part in the microparticle analysis apparatus 11 are the same as those in the first embodiment described above.

[Information Processor 12]

The information processor 12, which is connected to the microparticle analysis apparatus 11, includes: an analyzing part configured to calculate the property values of the microparticles from the measured impedance; and a determining part configured to determine whether the data of the measured impedance is derived from the microparticles. The specific configuration and operation of the analyzing part and the determining part are the same as those in the first embodiment described above. The analyzing part and the determining part may be provided in a single information processor or may be provided separately in different information processors.

[Server 13]

The server 13 is connected to the information processor 12 and an image display 14 through a network 15, and includes an information storage part. The server 13 manages various types of data uploaded from the information processor 12, and outputs them to the display 14 and the information processor 12 as requested.

[Display 14]

The display 14 displays the data of the impedance measured in the microparticle analysis apparatus 11, the property values of the microparticles calculated in the information processor 12, as well as the results determined in the determining part, and the like. The display may include an information input part through which a user selects and inputs the data to be displayed. In this case, the information inputted by the user is transmitted to the server 13 or the information processor 12 through the network 15.

The microparticle analysis system of the present embodiment, the determining part configured to determine whether the data of the impedance is derived from the microparticles is provided to reduce the influence of noise or the like. This results in accurate identification of the individual microparticles without using a labeling substance. In addition, various data analyses can be performed without applying loads to the microparticle analysis apparatus 11 and the information processor 12 by accumulating information in the server 13 and using it. This improves the data processing rate and facilitates data access, resulting in improved usability.

The configuration of the present embodiment can be also applied to the microparticle sorting device of the second embodiment described above, providing a microparticle sorting system. The configuration and effects other than those described above in the present embodiment are the same as those in the first embodiment described above.

Additionally, the present technology may also be configured as below.

(1)

A microparticle analysis apparatus including:

a sample channel configured to receive liquid containing a plurality of microparticles;

a first pair of electrodes configured to form an alternating electric field in at least a part of the sample channel;

a measuring part configured to measure impedance between the first pair of electrodes;

an analyzing part configured to calculate property values of the microparticles from the impedance measured in the measuring part; and a determining part configured to determine whether data of the impedance measured in the measuring part is derived from the microparticles.

(2)

The microparticle analysis apparatus according to (1), wherein the determining part detects passage of the microparticles through the alternating electric field from the data of the impedance, and makes determination based on a detection result.

(3)

The microparticle analysis apparatus according to (2), wherein the determining part detects the passage of the microparticles from a peak position and a peak height of conductance obtained from the impedance.

(4)

The microparticle analysis apparatus according to (2) or (3), wherein the determining part starts detecting the passage of the microparticles when a value/values of capacitance and/or conductance obtained from the impedance is/are over a threshold, and the determining part stops detecting the passage of the microparticles when the value/values is/are less than or equal to the threshold.

(5)

The microparticle analysis apparatus according to (4), wherein the determining part determines that the data of the impedance is derived from the microparticles only when the value/values of the capacitance and/or the conductance is/are over the threshold for a predetermined period.

(6)

The microparticle analysis apparatus according to any of (1) to (5), wherein the analyzing part calculates the property values for the data that is determined to be derived from the microparticles in the determining part.

(7)

The microparticle analysis apparatus according to (6), wherein the analyzing part calculates the property values by comparison or fitting of the data measured in the measuring part with a particular model.

(8)

The microparticle analysis apparatus according to (7), wherein the particular model is a dielectric relaxation phenomenon model based on a complex dielectric spectrum.

(9)

The microparticle analysis apparatus according to any of (1) to (8), including:

a sorting part configured to sort the microparticles based on the property values calculated in the analyzing part.

(10)

The microparticle analysis apparatus according to (9), including:

a second pair of electrodes configured to form an electric field downstream of an area where the alternating electric field is formed in the sample channel, wherein the electric field formed by the second pair of electrodes generates dielectrophoresis to change a flow direction of the microparticles.

(11)

The microparticle analysis apparatus according to (9) or (10), including:

two or more branched channels in communication with the sample channel, wherein the sorting part changes the flow direction of the microparticles, and the microparticles are introduced to any of the branched channels.

(12)

The microparticle analysis apparatus according to any of (1) to (11), wherein the sample channel includes a narrow part, and the first pair of electrodes are disposed to sandwich the narrow part.

(13)

The microparticle analysis apparatus according to any of (1) to (12), further including:

an imaging part configured to image the microparticles passing through the alternating electric field.

(14)

The microparticle analysis apparatus according to any of (1) to (13), wherein the microparticles are cells.

(15)

The microparticle analysis apparatus according to (14), wherein the property values include at least one value selected from the group consisting of membrane capacitance, conductivity of cytoplasm, and particle size.

(16)

The microparticle analysis apparatus according to (14) or (15), wherein the measuring part measures complex impedance at multiple points within a frequency range from 0.1 to 50 MHz.

(17)

A microparticle analysis system including:

a microparticle analysis apparatus including a sample channel configured to receive liquid containing a plurality of microparticles, a first pair of electrodes configured to form an alternating electric field in at least a part of the sample channel, and a measuring part configured to measure impedance between the first pair of electrodes; and an information processor including an analyzing part configured to calculate property values of the microparticles from the impedance measured in the measuring part, and a determining part configured to determine whether data of the impedance measured in the measuring part is derived from the microparticles.

(18) The microparticle analysis system according to (17), further including:
a display configured to display the property values of the microparticles calculated in the analyzing part of the information processor.

(19) The microparticle analysis system according to (17) or (18), further including:
a server including an information storage part configured to store the property values of the microparticles calculated in the analyzing part of the information processor.

REFERENCE SIGNS LIST 1, 11 microparticle analysis apparatus
2 sample channel
3a, 3b, 3c, 3d electrode
4 measuring part
5 determining part
6 analyzing part
7 information storage part
8 imaging part
9 determining-analyzing part
10 microparticle
12 information processor
13 server
14 display
15 network
21 narrow part
22 inflow channel part
23 outflow channel part
24 impedance measurement area
30 microparticle sorting device
31 sorting part
32 branched channel
100, 110 measurement system unit
200 flow forming system unit
201 pump
202 specimen introduction part
203 valve
300 control system unit

The invention claimed is:

1. A microparticle analysis apparatus comprising:
a sample channel configured to receive liquid containing a plurality of microparticles;
a first pair of electrodes configured to form an alternating electric field in at least a part of the sample channel;
a measuring part configured to measure impedance between the first pair of electrodes;
an analyzing part configured to calculate property values of the microparticles from the impedance measured in the measuring part; and
a determining part configured to determine whether data of the impedance measured in the measuring part is derived from the microparticles;
wherein the determining part detects passage of the microparticles through the alternating electric field from the data of the impedance, and makes determination based on a detection result;
wherein the determining part starts detecting the passage of the microparticles when a value/values of capacitance and/or conductance obtained from the impedance is/are over a threshold, and the determining part stops detecting the passage of the microparticles when the value/values is/are less than or equal to the threshold.

2. The microparticle analysis apparatus according to claim 1, wherein the determining part detects the passage of the microparticles from a peak position and a peak height of conductance obtained from the impedance.

3. The microparticle analysis apparatus according to claim 1, wherein the determining part determines that the data of the impedance is derived from the microparticles only when the value/values of the capacitance and/or the conductance is/are over the threshold for a predetermined period.

4. The microparticle analysis apparatus according to claim 1, wherein the analyzing part calculates the property values for the data that is determined to be derived from the microparticles in the determining part.

5. The microparticle analysis apparatus according to claim 4, wherein the analyzing part calculates the property values by comparison or fitting of the data measured in the measuring part with a particular model.

6. The microparticle analysis apparatus according to claim 5, wherein the particular model is a dielectric relaxation phenomenon model based on a complex dielectric spectrum.

7. The microparticle analysis apparatus according to claim 1, comprising:
a sorting part configured to sort the microparticles based on the property values calculated in the analyzing part.

8. The microparticle analysis apparatus according to claim 7, comprising:
a second pair of electrodes configured to form an electric field downstream of an area where the alternating electric field is formed in the sample channel,
wherein the electric field formed by the second pair of electrodes generates dielectrophoresis to change a flow direction of the microparticles.

9. The microparticle analysis apparatus according to claim 7, comprising:
two or more branched channels in communication with the sample channel,
wherein the sorting part changes the flow direction of the microparticles, and the microparticles are introduced to any of the branched channels.

10. The microparticle analysis apparatus according to claim 1, wherein the sample channel includes a narrow part, and the first pair of electrodes are disposed to sandwich the narrow part.

11. The microparticle analysis apparatus according to claim 1, further comprising:
an imaging part configured to image the microparticles passing through the alternating electric field.

12. The microparticle analysis apparatus according to claim 1, wherein the microparticles are cells.

13. The microparticle analysis apparatus according to claim 12, wherein the property values include at least one value selected from the group consisting of membrane capacitance, conductivity of cytoplasm, and particle size.

14. The microparticle analysis apparatus according to claim 12, wherein the measuring part measures complex impedance at multiple points within a frequency range from 0.1 to 50 MHz.

15. A microparticle analysis system comprising:
a microparticle analysis apparatus including
a sample channel configured to receive liquid containing a plurality of microparticles, a first pair of electrodes configured to form an alternating electric field in at least a part of the sample channel, and a measuring part configured to measure impedance between the first pair of electrodes; and an information processor including an analyzing part configured to calculate property values of the microparticles from the impedance measured in the measuring part, and a determining part configured to determine whether data of the impedance measured in the measuring part is derived from the microparticles;

wherein the determining part detects passage of the microparticles through the alternating electric field from the data of the impedance, and makes determination based on a detection result;

wherein the determining part starts detecting the passage of the microparticles when a value/values of capacitance and/or conductance obtained from the impedance is/are over a threshold, and the determining part stops detecting the passage of the microparticles when the value/values is/are less than or equal to the threshold.

16. The microparticle analysis system according to claim 15, further comprising:

a display configured to display the property values of the microparticles calculated in the analyzing part of the information processor.

17. The microparticle analysis system according to claim 15, further comprising:

a server including an information storage part configured to store the property values of the microparticles calculated in the analyzing part of the information processor.

* * * * *